United States Patent [19]

Pifferi

[11] 4,051,559

[45] Oct. 4, 1977

[54] TOTAL PROSTHESIS OF THE HIP

[75] Inventor: Marc Laurent Pifferi, Boissy Saint Leger, France

[73] Assignee: Mahay & Cie, France

[21] Appl. No.: 719,391

[22] Filed: Sept. 1, 1976

Related U.S. Application Data

[63] Continuation-in-part of Ser. No. 643,406, Dec. 22, 1975, abandoned.

[30] Foreign Application Priority Data

Dec. 27, 1974  France .................................. 74.42974

[51] Int. Cl.² ................................................. A61F 1/24
[52] U.S. Cl. .................................. 3/1.912; 128/92 C; 128/92 CA
[58] Field of Search .................................. 3/1.9–1.913, 3/1; 128/92 C, 92 CA, 92 R, 92 BA

[56] References Cited

U.S. PATENT DOCUMENTS

| 2,627,855 | 2/1953 | Price .............................. 128/92 BA |
| 3,067,740 | 12/1962 | Haboush .......................... 128/92 CA |
| 3,781,918 | 1/1974 | Mathys ................................. 3/1.91 |
| 3,818,512 | 6/1974 | Shersher .............................. 3/1.912 |
| 3,863,273 | 2/1975 | Averill ................................. 3/1.91 |
| 3,894,297 | 7/1975 | Mittelmeier et al. ...................... 3/1 |
| 3,903,549 | 9/1975 | Deyerle .............................. 3/1.912 |
| 3,924,275 | 12/1975 | Heimke et al. ...................... 3/1.912 |
| 3,965,490 | 6/1976 | Murray et al. ...................... 3/1.913 |
| 3,987,499 | 10/1976 | Scharbach et al. .................. 3/1.913 |

*Primary Examiner*—Ronald L. Frinks
*Attorney, Agent, or Firm*—Jacobs & Jacobs

[57] ABSTRACT

A total prosthesis of the hip has a cotyloid portion to be inserted in the hip bone and a cephalic portion to be inserted in the femur, the cephalic portion fitting into the cotyloid portion, and the cephalic portion has a cylindrical helically threaded femoral shank portion to be screwed into the femur and a flat abutment surface perpendicular to the axis of the threaded portion for abutment against a correspondingly prepared surface of the bone.

8 Claims, 8 Drawing Figures

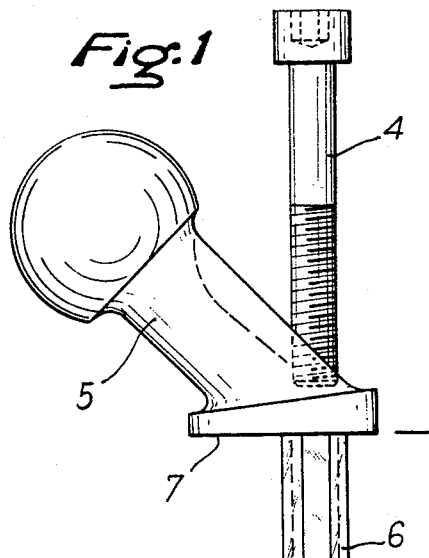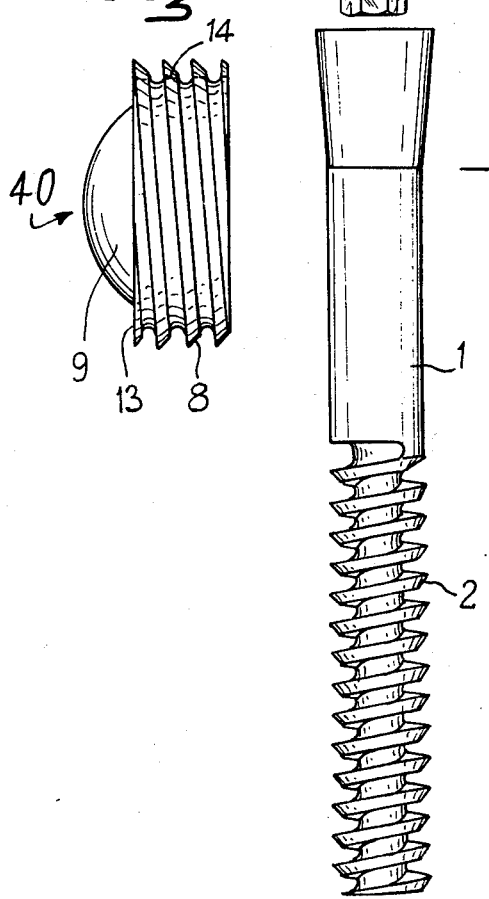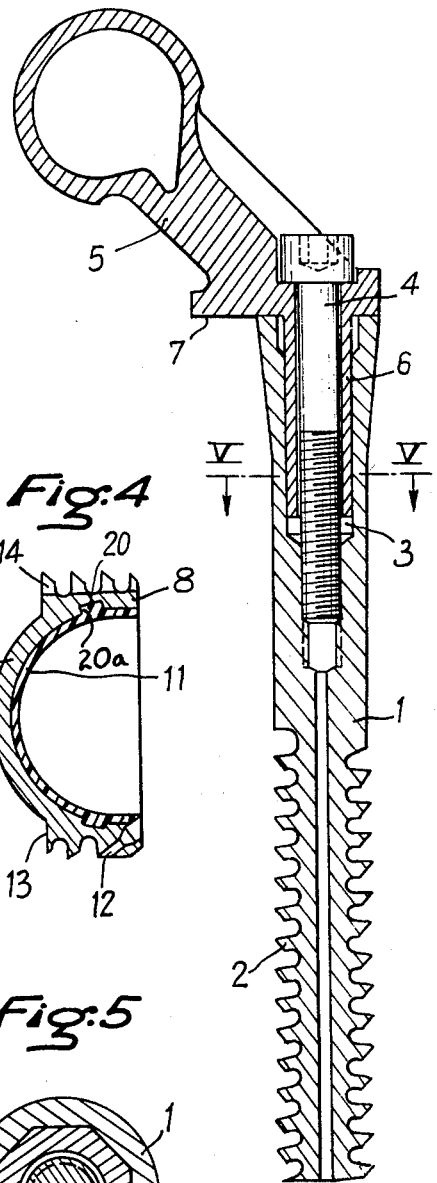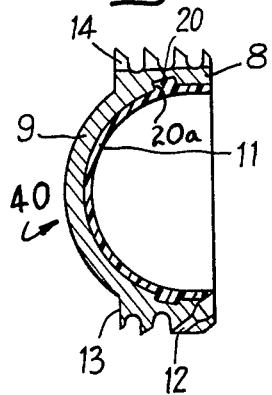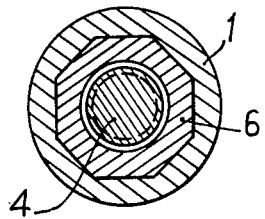

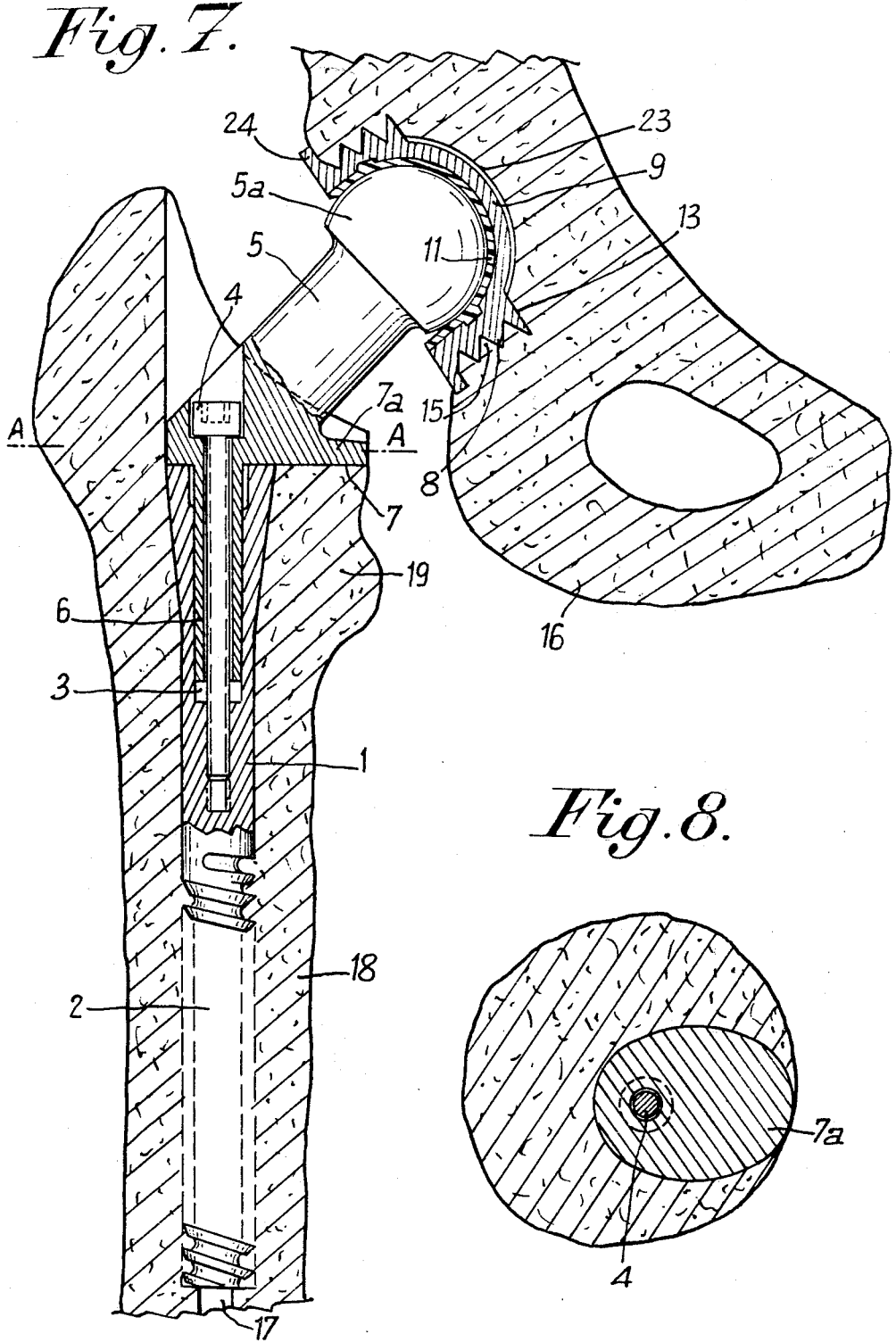

TOTAL PROSTHESIS OF THE HIP

This application is a continuation-in-part of my co-pending application Ser. No. 643,406, filed Dec. 22, 1975, now abandoned.

The present invention relates to total prostheses of the hip.

There are numerous types of total prostheses of the hip which are customarily designated by the name of the surgeon who devised them, namely Merle d'Aubigne's prosthesis, Thompson's prosthesis, MacKee's prosthesis, etc. These devices consist of a cephalic prosthesis which is fastened in the femur and of a cotyloid prosthesis which is fastened in the bone of the hip. This fastening is generally effected by cement, the bone being worked to provide a recess having the shape of the prosthesis within which the latter is fastened by the cement.

This method has one important drawback which results from the fact that the cement reacts with the bone tissue.

It has already been proposed to produce prostheses without cement for the femoral part of the cephalic prosthesis, said femoral part being smooth and inserted as is into the bone. However, in this case it is necessary to await the formation of the bone callus before any weight is placed on the prosthesis, which takes a very long time (up to 6 or 8 months) and results in very difficult rehabilitation.

An object of the present invention is a total prosthesis of the hip which makes it possible to avoid the drawbacks of the prior art prostheses.

Another object of the invention is to provide a total prosthesis of the hip that is fastened to the bone without any cement and can be placed under weight practically immediately.

The total prosthesis of the hip of the present invention comprises a cotyloid portion to be inserted in the hip and a cephalic portion to be carried by the femur, the cephalic portion fitting into the cotyloid portion to form a hip joint. The cephalic portion has a cylindrical shank portion depending therefrom that is threaded on the outside for screwing into a tapped bore in the medullar canal of the femur bone. The cephalic portion has a resting and abutment surface which is flat and is perpendicular to the axis of the tapped bore and is intended to come against a surface of the femur that has been prepared in corresponding manner.

The cotyloid portion is preferably outwardly cylindrical and threaded, so that it may be inserted in the hip bone by screwing, and has a resting and abutment surface which is flat and perpendicular to the axis of the thread, and is intended to abut against a bone surface prepared in corresponding manner.

The invention also relates to the method of inserting the prosthesis which consists in tapping the bones in a manner corresponding to the threads of the prosthesis and in reaming them over the untapped portions so as to define abutment surfaces and then putting the cephalic and cotyloid prostheses in position by screwing and abutment of the resting surfaces.

Preferably, the cephalic portion is formed of two parts, a cylindrical femoral portion, threaded for its insertion in the femur by boring and tapping of the medullar canal and a cephalic part, formed of an arm bearing at one end the ball which is inserted in the cotyloid portion and, on the other end, a diaphyseal resting surface perpendicular to the axis of a cylindrical sleeve which is eccentric with respect to the diaphyseal resting surface, said sleeve fitting in a bore hole of the same cross section provided in the axis of the femoral part. The locking of the cephalic part in angular position is obtained by hollowing and boring the end of the femur (greater trochanter) so as to define a flat stop surface perpendicular to the axis of the femoral tapping and having a contour which accurately corresponds to that of the diaphyseal resting surface of the cephalic part. All movement of rotation of the cephalic part is thus made impossible, while at the same time the placing thereof in the desired angular position is assured.

The invention also relates to the following arrangements:

1. The cotyloid portion is of metal and is covered on the inside with a plastic cup held in position by an annular portion which is inserted into a corresponding groove of the cotyloid portion.

2. The cotyloid portion is formed of a threaded portion of a height less than the total height of the part and the bottom of which has the shape of a dome.

3. The cotyloid portion bears an outer support shoulder of larger diameter than the diameter of the threaded portion.

4. At least one oblique drill hole is preferably provided in the cotyloid portion for the putting in position of screws which penetrate into a thick portion of the bone of the hip in order to complete the attachment of the cotyloid portion.

5. The cephalic portion is formed of two parts, a femoral part which is threaded for its insertion into the femur and a cephalic part, the latter bearing a cylindrical sleeve which may carry notches or the equivalent, the sleeve fitting in a drill hole of the same shape and section as the femoral part, while the notches, when present, cooperate with corresponding notches on the said femoral part, the assembly being locked in the selected angular position by a screw which passes through said sleeve and is threaded into the femoral part.

6. The cephalic part bears a diaphyseal resting surface perpendicular to the axis of the femoral part.

7. The axis of the cylindrical sleeve of the cephalic part is eccentric with respect to the diaphyseal resting surface, and the end of the femur is prepared so as to define a flat stop surface perpendicular to the axis of the threaded sleeve and having a contour which accurately corresponds to that of the diaphyseal resting surface of the cephalic part, thereby locking the assembly in the desired angular position.

8. The threaded portion of the cephalic part bears recesses into which the claws of a screwing tool can be inserted.

9. For a range of prostheses of different sizes, the cephalic heads, the cotyloid cups, and the sleeves and recesses of the cephalic and femoral parts, as well as their fastening screws, have the same dimensional characteristics, thus assuring their interchangeability.

The invention is illustrated in the accompanying drawing in which:

FIG. 1 is an exploded side view of the cephalic portion of a prosthesis in accordance with the invention;

FIG. 2 shows, in side view, the cotyloid portion of the prosthesis;

FIGS. 3 and 4 are views in longitudinal section of the cephalic and cotyloid portions of the prosthesis;

FIG. 5 is a section along the line V—V of FIG. 3;

FIG. 7 shows, in section, another embodiment of the invention; and

FIG. 8 is a sectional view along the line A—A of FIG. 7.

Figure 6:
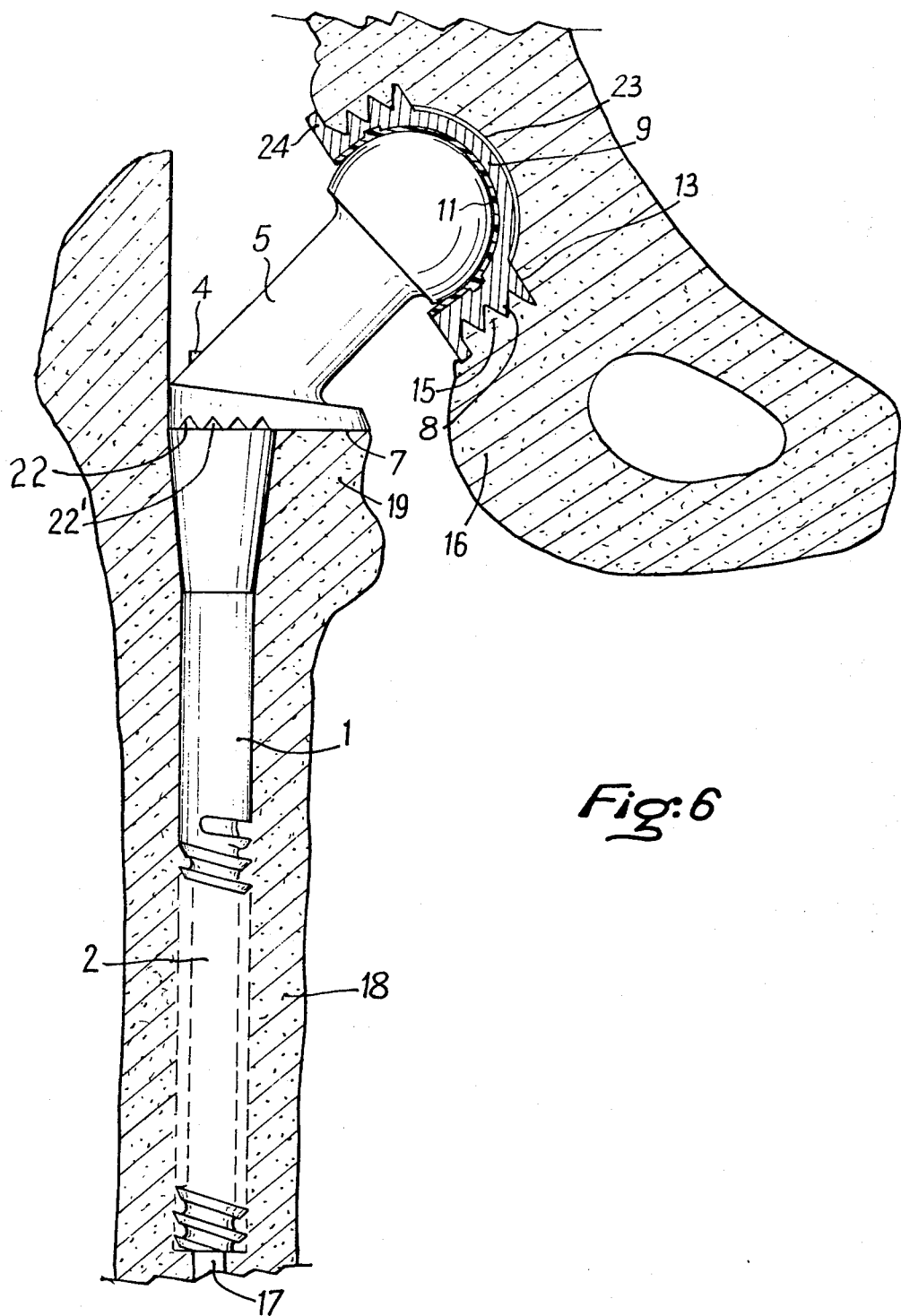
FIG. 6 shows, in section, another embodiment of the prosthesis in position in the bones.

Referring to these Figures, it is seen that the total prosthesis in accordance with the invention is composed of a cephalic portion 5, a femoral shank 1, and a cotyloid portion 40.

The femoral part or shank 1 is threaded in its lower portion 2 with a thread of a large relief. The upper portion of shank 1 is provided with a cylindrical recess 3 having a cross section of a regular polygon into which fits the sleeve 6 of corresponding shape of the cephalic portion 5. In the example shown in FIGS. 1-5, the cross section of recess 3 is octagonal and the head portion 5 can assume eight different angular positions with respect to the femoral part 1. Alternatively, recess 3 can be provided with a plurality of notches or grooves (not shown) into which fits a correspondingly shaped sleeve 6. Furthermore, in another alternative embodiment, diaphyseal part 7 of the cephalic portion 5 can be provided with radial notches 22 (FIG. 6) and the upper face of the shank 1 (FIG. 6) is provided with mating teeth 22'.

The cephalic portion 5 bears, furthermore, a diaphyseal surface provided by the underside of diaphyseal part 7, which is perpendicular to the axis of the shank 1. A screw 4 connects the femoral shank 1 and the cephalic portion 5 tightly together (FIG. 3).

The cotyloid portion 40 (FIGS. 2 and 4) is formed of a short threaded cylindrical section 8 on top of which is a dome 9, the assembly being spherically hollowed out on its inside and provided with a plastic cup 11. The plastic cup bears an annular protrusion 20 corresponding to an annular groove 20a in a spherical portion 10, which assures the holding of the cup 11 in position after it has been forceit into place.

Obligue lateral drill holes 12 may be provided for the passage of fastening screws into the bone of the hip at the places where the latter has excess thicknesses.

As shown in FIG. 6, the cotyloid portion 40 may have an abutment shoulder 24 which comes to rest against the outer face of the pelvis.

The rear face 13 of the thread 8 forms a locking stop for the cotyloid portion 40, which furthermore has longitudinal notches 14 to enable cotyloid portion 40 to be screwed into place, using a tool having claws which are inserted into said notches. Notches 14 may alternatively be provided in the shoulder 24 (FIG. 6).

The putting in place of the prosthesis is illustrated in FIG. 6. The bone 16 of the hip is tapped at 15 over the height of the thread 8. The bottom of the drilled internal thread is reamed so as to define the stop surface of the prosthesis and the bottom of the acetabulum 23 is reamed. The cotyloid portion 40 of the prosthesis is then screwed into place until its rear face 13 comes against the corresponding face of the bone. Oblique locking screws may be inserted in the lateral holes 12 (FIG. 4). The shoulder 24 is brought against the surface of the bone 16.

The medullar canal 17 of the femur 18 is bored and tapped with an internal thread corresponding to the thread of the femoral portion 1 of the prosthesis and the end 19 of the femur is sawed perpendicular to the tapping so as to define a resting surface for the diaphyseal part 7 of the cephalic portion 5. The latter is inserted in the femoral part 1 in the selected angular position, and fastened by the screw 4.

It should be noted that the plastic cup 11 may be shaped in such a manner as to provide a prosthesis of the so-called "retention" type.

In the embodiments of the invention described in FIGS. 1-6, the cephalic portion is formed of two parts which are connected by a screw and can be locked in relative angular position by means of notches or the equivalent. This arrangement may not assure a rigorously fixed angular positioning of the cephalic portion, and it is relatively difficult to use upon the putting of the prosthesis in place. The embodiment of the invention shown in FIGS. 7 and 8 represent significant improvements.

Referring to these FIGS. 7 and 8, it is seen that the femoral shank 1 has a femoral portion 2 which is cylindrical and threaded for its insertion into the femur 18 by boring and tapping the medullar canal 17, and of a cephalic portion 5 having a ball 5a which is adapted to be inserted in the cotyloid portion of the prosthesis, and a shoulder 7a the lower face of which forms a diaphyseal part 7 providing a resting surface which is perpendicular to the axis of the sleeve 6. Sleeve 6 is cylindrical and of circular section and terminates the part 5. The sleeve 6 is eccentric with respect to the diaphyseal surface, whose outer contour is preferably ovoid, as shown in FIG. 8. The sleeve 6 fits in the drill hole 3 provided in the axis of the femoral part 1.

In order to put the prosthesis of FIGS. 7 and 8 in place, the upper end of the femur is worked in the manner shown in the FIGS. 7 and 8, that is to say hollowed and bored, so as to form a recess having the contour of the shoulder 7a, said recess being terminated by a flat thrust face perpendicular to the axis of the drilling of the medullar canal 17, on which flat face the diaphyseal surface or diaphyseal part 7 comes to rest. As the contour of the recess which is thus hollowed out in the bone is identical to the contour of the shoulder 7a, the cephalic part 5, once put in place in the femoral part 1 and screwed by the screw 4, is locked in the proper angular position and is incapable of any rotation.

In a preferred embodiment, the femoral part 1 has a diameter of about 14 mm at its uppermost part, which tapers slightly to a diameter of about 10 mm at the top of the cylindrical shank. The distance from the axis of femoral part 1 to the edge of shoulder 7a is about 20 mm, so that the diaphyseal part 7 extends about 13 mm beyond the top of the femoral part 1. An extension of about 10 to about 16 mm would also be suitable.

The prosthesis of the invention has great advantages; in addition to the ease of putting it in place and anchoring it, it avoids any bursting forces on the femur such as those produced by all shanks of conical shape which must be inserted by force. Now these bursting forces cause necroses, and instead of obtaining rehabilitation of the bone and a rejuvenation of the bone tissues there is frequently noted a recession of the bone tissue, so that after a certain period of time the prosthesis no longer holds and tends to loosen.

Moreover, the forces due to the weight of the body are transmitted along the axis of the medullar canal of the femur and resolve themselves into forces of compression on the surface 7 and a force of traction or extension on the shaft 2 of the femoral part; thus on the one hand flexural forces on the femoral part 1 are practically eliminated, which forces cause breaks of prothesis shanks and abnormal fatigue of the bone and, on the other hand, the weight of the body does not result in any bursting force on the femur 18.

It can therefore be seen that the prosthesis of the invention gives particularly satisfactory results and, in particular, that it is possible for patients to get up a few days after the operation, which avoids, on the one hand, lengthy periods of hospitalization and, on the other hand, difficult and slow periods of rehabilitation.

From the foregoing description, it is evident that the invention provides a total prosthesis of the hip, the putting into place of which does not require the use of any cement while permitting immediate placing under load, the stresses being transmitted by the abutment surfaces of the parts to the bones.

Furthermore:

The bones are only slightly cut into, particularly the bone of the hip, as a result of the small height of threading of the cotyloid part bearing a dome on top;

the design of the cephalic part avoids the rubbing of metal on metal while assuring the strength of the metal. If desired, the cephalic part may be made wholly of plastic;

the diameters of the cotyloid spherical cup and of the cephalic head will preferably be identical for all dimensions of prostheses (for instance 35 mm), as well as the dimensional characteristics of the sleeve 6 and the recess 3, as well as the screws 4. In this way, parts 4, 5 and 40 are standardized, and the only variable will be the length of threaded portion 2 of shank 1, since sleeve 6 will fit into recess 3 of each shank 1. Hence, the various parts will be interchangeable and fit each other, whatever the dimension of part 2. In this way the surgeon can select the femoral part 1, the cephalic part 5 and the cotyloid portion 40 which are best suited for each patient, and the range of prostheses which can be produced is considerably increased for a given number of parts or molds;

the prosthesis is particularly strong due to its design, and the diaphyseal resting surface perpendicular to the axis of the shank assures the best transmission of forces.

The prosthesis will be preferably made of chrome cobalt alloy, but any suitable alloy can be employed.

In the foregoing description the sleeve 6 and the housing 3 have a polygonal (octagonal) section. It would be equivalent to develop them in the form of fluted cylinders or cylinders with longitudinal grooves or by notches 22 on the faces perpendicular to the axis of the shank. Any known means which assures a multiplicity of relative angular positions for the femoral and cephalic parts without any rotation being possible after the putting in place thereof may be used.

What is claimed is:

1. In a total prosthesis of the hip, comprising a cotyloid portion adapted to be inserted in the hip bone and a cephalic portion adapted to be inserted in the femur, the cephalic portion fitting into the cotyloid portion, the improvement in which said cephalic portion comprises a femoral part having a cylindrical externally helically threaded shank portion adapted to be screwed into the medullar canal of the femur and a cephalic part having a base member the underside of which having a flat diaphyseal resting and abutment surface adapted to abut against a bone surface prepared in corresponding manner, an arm on said base member terminating in a ball means for insertion into said cotyloid portion and a sleeve depending perpendicularly from and eccentric with respect to the diaphyseal resting surface, said sleeve fitting in a bore of the same cross section provided in said femoral part, and means for securing said femoral part to said cephalic part.

2. The prosthesis according to claim 1, wherein said diaphyseal resting surface is ovoid.

3. The prosthesis according to claim 1, wherein the sleeve is cylindrical and is fitted coaxially in said femoral part.

4. The prosthesis according to claim 1, wherein said securing means is a screw means passing through said sleeve and being screwed into the femoral part.

5. The prosthesis according to claim 4, wherein the cephalic portion includes cooperating means for preventing angular movement of the cephalic part relative to the femoral part, the assembly being locked in the selected angular position by said screw means passing through said sleeve and being screwed into the femoral part.

6. The prosthesis according to claim 5, wherein said cooperating means is provided by said sleeve and said recess being of substantially identical polygonal cross section.

7. The prosthesis according to claim 6, wherein said cooperating means further includes notches in one of the cephalic parts and the femoral part and mating teeth in the other of the parts.

8. A process for the putting in place of the total prosthesis of the hip of claim 1, wherein the medullar canal is tapped with a cylindrical, helical thread, the end of the femur is hollowed out and bored to form a recess having a flat surface corresponding to said diaphyseal surface that is perpendicular to the axis of the cylindrical thread, said axis being eccentric with respect to the flat surface, the femoral part is screwed into the cylindrically threaded medullar canal, the sleeve of the cephalic part is inserted into the bore of the femoral part, and the cephalic part is screwed into place with the disphyseal resting surface thereof firmly contacting said flat recess in the femur.

* * * * *